US010954185B2

(12) United States Patent
Srinivasan et al.

(10) Patent No.: US 10,954,185 B2
(45) Date of Patent: *Mar. 23, 2021

(54) ECO-FRIENDLY PROCESS FOR HYDROGENATION OR/AND HYDRODEOXYGENATION OF ORGANIC COMPOUND USING HYDROUS RUTHENIUM OXIDE CATALYST (71) Applicant: Council of Scientific & Industrial Research, New Delhi (IN)

(72) Inventors: Kannan Srinivasan, Bhavnagar (IN); Sreedhar Gundekari, Bhavnagar (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/766,454

(22) PCT Filed: Oct. 7, 2016

(86) PCT No.: PCT/IN2016/050340
§ 371 (c)(1),
(2) Date: Apr. 6, 2018

(87) PCT Pub. No.: WO2017/060922
PCT Pub. Date: Apr. 13, 2017

(65) Prior Publication Data
US 2019/0084918 A1 Mar. 21, 2019

(30) Foreign Application Priority Data
Oct. 7, 2015 (IN) .............................. 3219DEL2015

(51) Int. Cl.
| C07C 209/72 | (2006.01) |
| C07C 29/141 | (2006.01) |
| C07C 29/145 | (2006.01) |
| C07C 29/20 | (2006.01) |
| C07C 41/20 | (2006.01) |
| C07C 5/03 | (2006.01) |
| C07C 51/36 | (2006.01) |
| C07C 29/19 | (2006.01) |
| C07B 35/02 | (2006.01) |
| C07D 307/44 | (2006.01) |
| C07D 307/33 | (2006.01) |
| B01J 23/46 | (2006.01) |

(52) U.S. Cl.
CPC ........... *C07C 209/72* (2013.01); *B01J 23/462* (2013.01); *C07B 35/02* (2013.01); *C07C 5/03* (2013.01); *C07C 29/141* (2013.01); *C07C 29/145* (2013.01); *C07C 29/19* (2013.01); *C07C 29/20* (2013.01); *C07C 41/20* (2013.01); *C07C 51/36* (2013.01); *C07D 307/33* (2013.01); *C07D 307/44* (2013.01); *C07C 2523/46* (2013.01); *C07C 2601/14* (2017.05); *Y02P 20/584* (2015.11)

(58) Field of Classification Search
CPC ..... C07B 35/02; C07C 209/72; C07C 29/141; C07C 29/145; C07C 29/19; C07C 29/20; C07C 41/20; C07C 5/03; C07C 51/36
See application file for complete search history.

(56) References Cited

U.S. PATENT DOCUMENTS

| 5,614,646 | A | 3/1997 | Wettling et al. |
| 5,689,003 | A | 11/1997 | Beatty et al. |
| 6,441,255 | B1 | 8/2002 | Haas et al. |
| 6,462,206 | B1 | 10/2002 | Bullock et al. |
| 6,649,211 | B2 * | 11/2003 | Lyons ..................... C23C 16/04 427/126.5 |
| 10,221,149 | B2 * | 3/2019 | Srinivasan ........... C07D 307/33 |
| 2007/0066849 | A1 | 3/2007 | Vedage et al. |
| 2012/0123142 | A1 | 5/2012 | Dyke et al. |
| 2013/0296579 | A1 | 11/2013 | Rode et al. |

FOREIGN PATENT DOCUMENTS

| CN | 1170630 A * | 1/1998 | .......... C07C 209/72 |
| CN | 1970528 A * | 5/2007 | .......... C07C 209/72 |
| WO | 2016056030 A1 | 4/2016 | |
| WO | 2017060922 A1 | 4/2017 | |

OTHER PUBLICATIONS

Galletti et al., "A sustaniable process for the production of gamma-valerolactone by hydrogenation of biomass-derived levulinic acid," Green Chemistry, 2012, 14, 688. (Year: 2012).*
European Patent Office Search Report and Written Opinion dated Feb. 23, 2017 in reference to PCT/IN2016/050340 filed Oct. 7, 1016.
Galletti, et al.; "A Sustainable Process for the Production of γ-Valerolactone by Hydrogenation of Biomass-Derived Levulinic Acid"; Green Chemistry; 2012; 14; pp. 688-694.
Geilen, et al.; "Selective and Flexible Transformation of Biomass-Derived Platform Chemicals by a multifunctional Catalytic System"; Angew. Chem. Int. Ed.; 2010; 49; pp. 5510-5514.
Koopman, et al.; "Induction Effects in Liquid Phase Hydrogenation Catalyzed by Ruthenium on Carbon"; Colloids and Surfaces; 3; Jan. 1, 1981; pp. 1-12.
Ortiz-Cervantes, et al.; "Hydrogenation of Levulinic Acid to γ-Valerolactone Using Ruthenium Nanoparticles"; Inorganica Chimica Acta, Elsevier BV, NL; vol. 39; Dec. 7, 2012; pp. 124-128.

(Continued)

*Primary Examiner* — Rosalynd A Keys
(74) *Attorney, Agent, or Firm* — Dinsmore & Shohl, LLP (57) ABSTRACT The invention discloses a process for hydrogenation (alkenes, carbonyl compounds and aromatics) and hydrodeoxygenation (methoxy phenols) of organic molecules using hydrous ruthenium oxide (HRO) and its supported form as a recyclable heterogeneous catalyst in aqueous medium with good yield of desired products (70-100%) under mild reaction conditions.

12 Claims, 2 Drawing Sheets

(56) References Cited

OTHER PUBLICATIONS

Jae, et al.; "The Role of Ru and RuO2 in the Catalytic Transfer Hydrogenation of 5-Hydroxymethylfurfural for the Production of 2,5-Dimenthylfuran"; ChemCatChem; 2014; 6; pp. 848-856.

Tan et al.; "Water-Promoted Hydrogenation of Levulinic Acid to γ-Valerolactone on Supported Ruthenium Catalyst"; ChemCatChem, 2015; 7; pp. 508-512.

Kuhn, et al.; "Ruthenium Catalysed Hydrogenation of Oxygen Functionalized Aromatic Compounds in Water"; ChemCatChem; 2013; 5; pp. 3241-3248.

Tomishige, et al.; "Selective Production of Cyclohexanol and Methanol from Guaiacol over Ru Catalyst combined with MgO"; Green Chem.; 2014; 16; pp. 2197-2203.

Chaudret, et al.; "How to Modulate Catalytic Properties in Nanosystems: The Case of Iron-Ruthenium Nanoparticles"; ChemCatChem; 2014; 6; pp. 1714-1720.

Sreedhar Gundekari and Kannan Srinivasan, "Hydrous ruthenium oxide: A new generation remarkable catalyst presursor for energy efficient and sustainable production of γ-valerolactone from levulinic acid in aqueous medium," Applied Catalysis A, General, 569, 2019, pp. 117-125.

\* cited by examiner

ECO-FRIENDLY PROCESS FOR HYDROGENATION OR/AND HYDRODEOXYGENATION OF ORGANIC COMPOUND USING HYDROUS RUTHENIUM OXIDE CATALYST

FIELD OF THE INVENTION

The present invention relates to an eco-friendly process for hydrogenation of organic molecules using hydrous ruthenium oxide (HRO) and its supported forms as efficient and recyclable heterogeneous catalyst. More particularly, the invention relates to hydrogenation of organic molecules such as alkenes, carbonyl compounds and substituted aromatics and also for the processes that involve hydrodeoxygenation, for example, lignin derived aromatics (methoxy phenols).

BACKGROUND OF THE INVENTION

Catalytic hydrogenation is an important transformation in organic synthesis and many reports and processes are available and practiced using homogeneous and heterogeneous catalysts. Continued research is attempted both by academicians and industrial researchers on the preparation and exploration of different catalytic materials for efficient hydrogenation reactions. Depletion of fossil resources poses many countries to work on biomass as a viable substitute for making chemicals and fuels. Transformation of biomass building blocks mainly invokes dehydration, hydrogenation and hydrodeoxygenation reactions. Thus, catalytic hydrogenation and hydrodeoxygenation are important both in conventional petroleum based as, well renewable biomass-based industries. Developing efficient, recyclable, inexpensive catalyst to enable these reactions is a challenge.

Generally d-block metals such as Ni, Mo, Ir, Co, Rh, Cu, Pd, Ru, Pt and Au are explored for the hydrogenation reactions and among them Pt, Pd, Ru and Au are comparatively more active. For gas phase hydrogenation reactions, Pt and Pd have good catalytic activity while in liquid phase Ru is more catalytically active, preferably in aqueous medium, where it exhibit good stability as well.

F. E. Kuhn et al. in their paper titled "Ruthenium catalysed hydrogenation of oxygen functionalized aromatic compounds in water" in *ChemCatChem*. 2013, 5, 3241-3248 reported that ruthenium complex containing sulfonated bis-N-heterocyclic carbene (NHC) ligand as an active catalyst for hydrogenation of lignin derived aromatics at 40 bar $H_2$ at 60° C. in water (0.1M KOH solution). The drawbacks of the work are high pressure, longer reaction time, poor selectivity, and necessity of additional chemicals. In addition, the complexes are homogeneous and hence not recyclable and poses separation and disposal problems.

R.P.Beatty et al. in a U.S. Pat. No. 5,689,003 have disclosed bulkier ruthenium complex $Ru(n^3-C_6H_8—PCy_2)(PCy_3)Cl$ as catalyst for the conversion of nitriles and nitro compounds to amines. The drawbacks of the work are high energy and chemical consumption for bulky catalyst synthesis, and necessity of additives. In addition, the complexes are homogeneous and hence not recyclable and poses separation and disposal problems.

W. Leitner et al. in their paper titled "Selective and flexible transformation of biomass derived platform chemicals by a multifunctional catalytic system" in *Angew. Chem. Int. Ed*. (2010) 49, 5510-5514 reported that Ru (PnOct$_3$) as active catalyst for the conversion of levulinic acid to γ-valerolactone at 160° C., 100 bar $H_2$ pressure in 18 h in presence of $NH_4PF_6$ as additive. The drawbacks of the work are high temperature, high pressure, longer reaction time and necessity of additional chemicals. In addition, the complexes are homogeneous and hence not recyclable and poses separation and disposal problems.

A.Dyke et al. in US Patent US 2012/0123142 A1 have disclosed hydrogenation of carbon-heteroatom double bond using bulkier ruthenium monosulfonated diamine complex as catalyst. The drawbacks are high energy and chemical consumption for bulky catalyst synthesis and are homogeneous and thus are not recyclable and poses separation and disposal problems.

R. M. Bullock et al. in U.S. Pat. No. 6,462,206 B1 have disclosed hydrogenation of ketones and aldehydes using organometallic ruthenium complexes, for example {[Cp*Ru(CO)$_2$]$_2$(μ-H)}$^+$OTf. The drawbacks of the work are longer reaction time, low yields, use of expensive chemicals for catalyst synthesis and use of hazardous organic solvents (dichloro benzene) in the reaction.

To avoid separation problem of catalysts from the reaction mixture other group of researchers have developed various ruthenium based heterogeneous hydrogenation catalysts in the last two decades.

T. Haas et al. in a U.S. Pat. No. 6,441,255 B1 disclosed hydrogenation of aldehydes and ketones using ruthenium supported on $TiO_2$, $SiO_2$, $ZrO_2$, MgO, and silicates. Among them, ruthenium supported on $TiO_2$ and $SiO_2$ catalysts showed longer shelf life (long term stability). The drawbacks of the work are poor selectivity of desired products and necessity of prior reduction of catalyst.

P. N. Rylander et al. in U.S. Pat. No. 3,177, 258 disclosed hydrogenation of different aliphatic and aromatic functional organic compounds using ruthenium along with another platinum group metal such as Pd, Pt and Rh supported carbon catalyst. The drawbacks of the work are poor selectivity of desired products and use of expensive other metals (Pd, Pt and Rh) along with Ru.

G.A. Vedage et al. in a U.S. Pat. No. 0,066,849A1 disclosed ruthenium supported lithium aluminate ($LiAl_5O_8$) as efficient hydrogenation catalyst for anilines to cyclohexylamines without prior reduction of catalyst. The drawback of the work is high energy requirement for catalyst support synthesis ($LiAl_5O_8$) and no mention on the catalyst recyclability.

C.S. Tan et al. in their paper titled "Aromatic hydrogenation of benzyl alcohol and its derivatives using compressed $CO_2$/water as the solvent" in *Green Chem.* (2012) 14, 682-687 reported a green approach for hydrogenation of benzyl alcohol and benzaldehyde to cyclohexanemethanol using 5% Ru/MCM-41at 30-60 bar $H_2$ pressure for 5 h in aqueous medium. The drawbacks of the work are high energy and use of expensive chemicals for catalysts synthesis, and necessity of high temperature and pressure for the reaction.

K. Tomishige et al. in their paper titled "Selective production of cyclohexanol and methanol from guaiacol over Ru catalyst combined with MgO" in *Green Chem.* (2014) 16, 2197-2203 disclosed preparation of cyclohexanol and methanol from aqueous guaiacol using 5% Ru/C catalyst along with MgO and achieved >80% product yield at 160° C., 15 bar $H_2$ in 2 h. The catalyst was also tested for the conversion of phenol and catechol to cyclohexanol derivatives. The drawbacks of the work are necessity of additional co-catalyst (MgO), higher temperature and lesser selectivity of desired cyclohexanols.

B. Chaudret et al. in their paper titled "How to modulate catalytic properties in nanosystems: The case of iron-ruthenium nanoparticles" in *ChemCatChem*. 2013, 5, 3241-3248 reported preparation of ultra-small FeRu bimetallic nanoparticles by co-decomposition of two organometallic precursors namely {Fe[N(Si—(CH$_3$)$_3$)$_2$]$_2$}$_2$ and ($\eta^6$-1,5-cyclooctadiene)($\eta^6$-1,3,5-cyclooctatriene)ruthenium(0)(Ru(COD)(COT)) under H$_2$ at 150° C. in mesitylene. The synthesized fine bimetallic nanoparticles were applied for the preparation of ethyl benzene from styrene and 2-butanol from 2-butanone at room temperature, at 3 bar H$_2$ in 24 h. The drawbacks of the work are high energy and use of expensive chemicals for catalysts synthesis, longer reaction time and use of high boiling carcinogenic solvent (mesitylene) in the reaction.

A.M.R. Galletti et al. in their paper titled "A sustainable process for the production of γ-valerolactone by hydrogenation of biomass-derived levulinic acid" in *Green Chem.* (2012) 14, 688 disclosed performance of Ru/C catalyst along with combination of various heterogeneous acid co-catalysts and found that Amberlyst A70 as efficient co-catalyst that showed higher yield (99.5%) at 70° C., 5 bar H$_2$ within 3 h in aqueous medium. Further the two catalytic systems were applied for the conversion of ketones to alcohols such as 2-butanone and 2-pentanone to corresponding alcohols with 91-92% product yield at 70° C., 5 bar H$_2$ for 1 h in aqueous medium. The drawbacks of the process are necessity of large amount of acid co-catalyst (Amberlyst A70) and longer reaction time.

T. Wettling et al. in U.S. Pat. No. 5,614,646 disclosed selective hydrogenation of aromatic groups of organic molecules carrying at least one aromatic group and one epoxy group with hydrogen in the presence of a ruthenium-containing catalyst, in which invention used hydrous ruthenium oxide as catalyst at 250 bar. The drawbacks of the work are limited substrate scope, high pressure and lack in recyclability of catalyst.

Besides those cited above in the prior-art, many research groups and industries have reported several ruthenium catalytic systems for selective hydrogenation of organic molecules into variety of products using hydrogen. However, many reported catalytic systems have several drawbacks such as high energy and necessity of hydrogen for prior reduction of catalysts, additional expensive raw materials such as co-catalysts, ligands, supports, and additives and chemicals involved in the preparation of catalysts, metal leaching, poor selectivity of desired products, harsher reaction conditions (high temperature and pressure), and longer reaction time and often in organic solvents.

Kannan et al. in WO 2016/056030 disclosed efficient catalytic performance of hydrous ruthenium oxide (HRO; RuO$_2$.xH2O) for the selective hydrogenation of levulinic acid to γ-valerolactone. Although this work avoided many drawbacks mentioned above, it is very limited in substrate scope and industrial applicability without any flexibility on the control of hydrogen pressure.

To avoid or minimize the above mentioned drawbacks for hydrogenation reactions of organic molecules using reusable catalysts, in particular ruthenium based catalysts, it is mandatory to design and develop a catalyst that performs the reaction under near ambient or energy less intensive conditions in shorter time which is required in smaller quantity and is also recyclable and render good yield of the desired products. Furthermore, it is important to have a control on hydrogen pressure that in turn has significant implications on the product yield/selectivity pattern.

In the present invention, the utility of hydrous ruthenium oxide (HRO) and its supported forms as catalysts is disclosed for the transformation of many organic molecules comprising, but not limited to, alkenes, ketones and substituted aromatics that involves hydrogenation and lignin derived methoxy phenols that involves hydrodeoxygenation reaction in aqueous medium. The catalysts showed excellent activity for diverse substrates with high conversions of reactants and selectivity of the desired products.

OBJECTIVES OF THE INVENTION

The main objective of present invention is to provide an eco-friendly process for hydrogenation and hydrodeoxygenation of organic molecules using hydrous ruthenium oxide (HRO) and its supported forms as recyclable heterogeneous catalyst which obviates the drawbacks mentioned above.

Still another object of the present invention is to conduct the hydrogenation (or) hydrodeoxygenation reactions preferentially in aqueous medium Still another objective of the present invention is to provide a process where hydrogenation or/and hydrodeoxygenation reactions are conducted in a flow-controlled variable pressure mode to achieve better selectivity and would render safety.

Still another object of the present invention is to develop hydrogenation and hydrodeoxygenation processes in shorter reaction time and under mild reaction conditions (to have better energy efficiency) for industrially important molecules including bio-derived molecules.

SUMMARY OF THE INVENTION

The present invention relates to hydrogenation and hydrodeoxygenation of organic molecules using hydrous ruthenium oxide (HRO) and its supported form as efficient and recyclable heterogeneous catalyst in excellent yields (70-100%). More particularly, the invention involved hydrogenation of alkenes, carbonyl compounds and substituted aromatics and also for the processes that involve selective hydrodeoxygenation of lignin derived methoxy phenols. The reactions Were performed in a aqueous medium, at a temperature in the range of 25-200° C. and at a hydrogen pressure in the range of 2-50 bar, with ruthenium loading in the range of 0.1-0.7 wt. % with respect to reactants and the concentration of reactants in the range of 1-20 wt. % with respect to solvent and for the reaction time of 5 min to 10 h. Accordingly, the present invention provides a process for hydrogenation or/and hydrodeoxygenation of organic molecules using hydrous ruthenium oxide (HRO) comprising the steps: reacting the organic molecule with hydrogen in presence of hydrous ruthenium oxide (HRO) or its supported forms as efficient heterogeneous catalysts in aqueous medium while operating under mild reaction conditions at a temperature in the range of 25 to 200° C. and at a pressure in the range of 2 to 50 bar to obtain the desired products with excellent yields.

In an embodiment of the invention wherein the process comprising the following, steps:
   (i) mixing a reactant organic compound in-water at room temperature in the range of 24 to 28° C. in a reactor vessel to form a solution;
   (ii) adding catalyst to the solution obtained in step (i) to obtain a mixture and tightly close the reactor vessel to the head assembly of the reactor;
   (iii) maintaining the pressure and temperature of the reactor in a specific mode selected from mode (i) or (ii);
      mode (i) comprising:

a. purging $H_2$ into the mixture obtained in step (ii) at 1-2 bar for three times and adding $H_2$ to attain desired pressure ranging between 2 to 50 bar in the reactor vessel;
b. heating the reactor vessel to desired temperature ranging between 25 to 200° C. and stir the reaction mixture after attaining temperature at 600-1000 rpm for 5 min to 3 h;
mode (ii) comprising:
a. purging $H_2$ into the mixture obtained in step (ii) at 1-2 bar for three times and heating the reactor vessel to desired temperature ranging between 25 to 160° C.
b. adding $H_2$ continuously into the reactor, after attaining the desired temperature at a flow rate ranging 10-100 ml/min through a mass flow controller (MFC) while simultaneously stirring the reaction mixture at 600-1000 rpm for 30 min to 10 h
(iv) cooling down the reactor vessel to the temperature in the range 25 to 28° C. and release the unreacted $H_2$ and remove the vessel from the head assembly and separating the catalyst to obtain the product mixture;
(v) separating products from the product mixture obtained in step (iv) either via direct solvent evaporation or by extractive separation that can be reused and analysing the separated products both qualitatively and quantitatively.

In another embodiment of the invention wherein the reactant organic molecules are selected from a group consisting of alkenes, carbonyl compounds, aromatics;
(i) alkenes is selected from cyclohexene and α angelica lactone,
(ii) carbonyl compounds is selected from furfural, glucose, mannose, xylose, acetone, cyclohexanone, 2-butanone, 2-hexanone and methyl isobutylketone,
(iii) aromatic compound is selected from a group consisting of phenol, benzyl alcohol, anisole, aniline, methyl nicotinate, benzoic acid, benzaldehyde, benzoic acid, acetophenone, and
(iv) methoxy phenols are selected from guiacol, syringiol, 3-methoxy, phenol and 4-methoxyphenol.

In another embodiment of the invention wherein the supported hydrous ruthenium oxide (HRO) catalyst is selected from Na-β, H-β and $TiO_2$.

In yet another embodiment of the invention wherein the Ru content used with respect to reactants is ranging between 0.1-0.7 wt. %, preferably 0.2-0.35 wt. %.

In still another embodiment of the invention wherein reactants concentration vary in the range 1 to 20 wt. %, preferably in the range of 2 to 12.5 wt. %.

In another embodiment of the invention, wherein the conversion of reactants and yield of products are in the range of 0 to 100%, preferably in the range of 70 to 100%.

In another embodiment of the invention, wherein the methods adopted of adding hydrogen into the reactor for pressurizing influence the selectivity of the products, in particular for methoxy phenols.

In another embodiment of the invention, wherein the catalysts are reusable with similar activity.

DETAILED DESCRIPTION OF THE INVENTION

Figure 1:
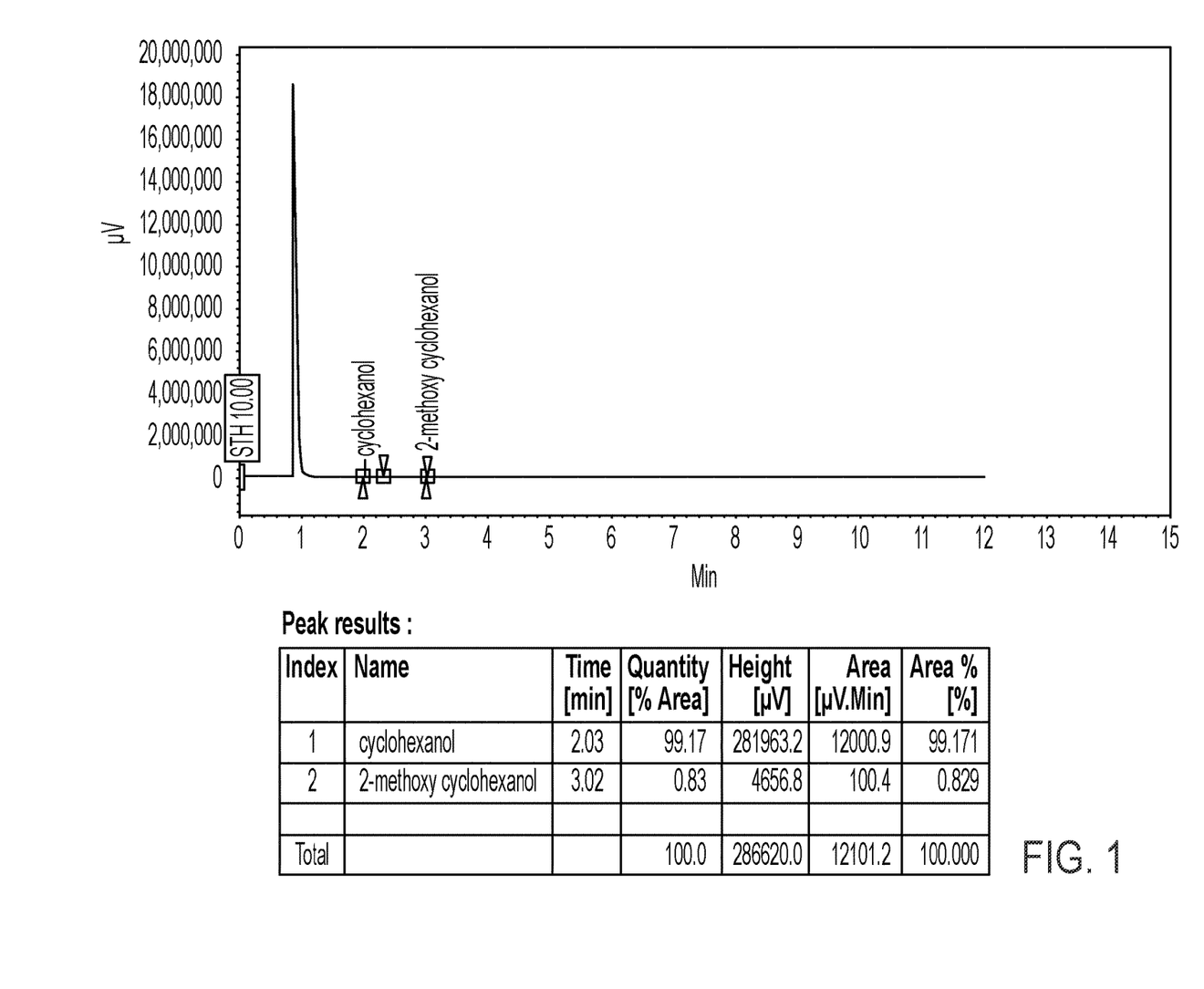
FIG. 1: GC profile of the product mixture from Example 31
Figure 2:
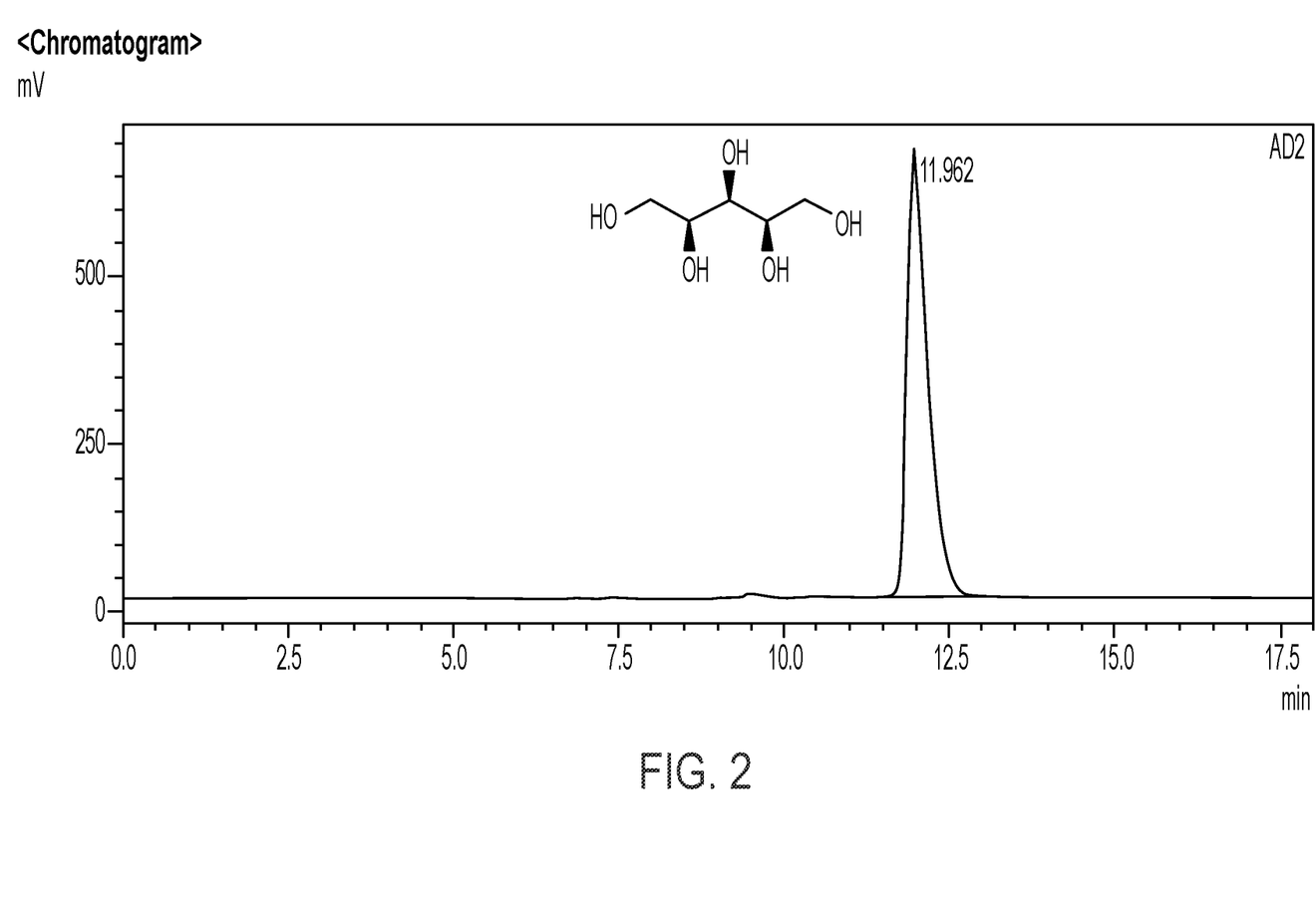
FIG. 2: UHPLC of the product mixture from Example 14

The present invention provides an eco-friendly process for hydrogenation of organic molecules using hydrous ruthenium oxide (HRO; $RuO_2.xH_2O$) or its supported form as a recyclable efficient catalyst. The organic molecule along with water were taken in a reaction vessel and a pre-calculated quantity of catalyst was added into the vessel. The latter was heated for varied period of time. The reaction was carried out in presence of hydrogen both in a fixed pressure mode and in continuous flow mode. After completion of the reaction, the catalyst was separated by using a centrifuge and the clear product mixture was analyzed by GC-MS and UHPLC. The catalyst provides selective hydrogenation of various organic molecules such as: (i) Hydrogenation of alkenes to alkanes; (ii) Hydrogenation of ketones/aldehydes to alcohols; (iii) Hydrogenation of aromatics and (iv) Hydrodeoxygenation of lignin derived methoxy phenols to cyclohexanols.

The present invention discloses a hydrogenation and hydrodeoxygenation of organic molecules using hydrous ruthenium oxide (HRO) and HRO/supports as efficient and recyclable heterogeneous catalysts in aqueous medium with excellent yields (70-100%) of products while operating under mild reaction conditions in shorter time.

The reactor was loaded with reactants, solvent (water), and catalysts at one time. The reaction was conducted at desired temperature and $H_2$ pressure with either fixed or flow-controlled variable pressure mode for a specified period of time. After completion of the reaction, reactor was cooled to room temperature and unconsumed hydrogen was released. The solid catalyst was separated by centrifugation and used for next cycle without any treatment. The liquid product mixture was quantified using ultra high-performance liquid chromatography (UHPLC), gas chromatography (GC), gas chromatography-mass spectrometry (GC-MS). The catalysts used in the invention are HRO and supported HRO. The HRO catalyst was prepared by using conventional precipitation method using NaOH or through a modified method using $CaCO_3$. Supported HRO catalysts (supports used are $TiO_2$ Na-β and H-β zeolites) were prepared by precipitation followed by impregnation using dilute $RuCl_3$ solution (0.001 M) and $CaCO_3$ as precipitating agent.

The present invention provides hydrogenation and hydrodeoxygenation of organic molecules using HRO and its supported form as catalysts in presence of a solvent selected from water alone. The reactions were performed at a temperature in the range of 25-200° C. and with a hydrogen pressure in the range of 2-50 bar, the ruthenium loading in the range of 0.1-0.7 wt. % with respect to reactants, the concentration of reactants is in the range of 1-20 wt. % with respect to solvent. The reaction progress was monitored at different time intervals in the range of 5 min to 10 h.

In particular, using alkene reactants, the reactions were performed at temperature in the range of 70-80° C. and with a hydrogen pressure in the range of 5-10 bar, the ruthenium loading in the range of 0.25-0.35 wt. % with respect to alkenes, the concentration of alkenes is 5 wt. % with respect to solvent and the reactions were monitored in the time interval in the range of 5 min to 1 h. A maximum conversion of alkenes and the yield of hydrogenated products were achieved using HRO and its supported form catalysts in aqueous medium under mild reaction conditions. 100% conversion of cyclohexene with 100% yield of cyclohexane was achieved using HRO catalyst (Table 1, entry 1, example 1). 100% conversion of α-angelica lactone (α-al) with 100% yield of γ-valerolactone (Gvl) was achieved using HRO/Na-β catalyst (Table 1, entry 2, example 2).

In particular, using carbonyl compounds as reactants, the reactions were performed at temperature in the range of 80-150° C. and with a hydrogen pressure in the range of 5-50 bar, the ruthenium loading in the range of 0.1-0.35 wt. % with respect to carbonyl compounds, the concentration of carbonyl compounds is in the range of 1.25-12.5 wt. % with respect to solvent and monitored in the time interval in the range of 10 min to 3 h.

A maximum conversion of ketones and the yield of corresponding alcohol products were achieved using HRO and its supported form catalysts in aqueous medium under mild reaction conditions. 100% conversion of ketones such as 2-hexanone, cyclohexanone, methyl isobutyl ketone (MIBK), 2-butanone and acetone with 100% yield of corresponding alcohols were achieved (Table 2, entry 1-8, example 3-10).

A maximum conversion of aldehydes and the yield of corresponding alcohol products were achieved using HRO supported catalysts in aqueous medium under mild reaction conditions. 100% conversion of aldehydes such as furfural, glucose, xylose and mannose with 100% yield of corresponding alcohols were achieved (Table 3, entry 1-9, example 11-19).

In particular, using substituted aromatics, the reactions were performed at temperature in the range of 70-120° C. and with a hydrogen pressure in the range of 10-20 bar, the ruthenium loading in the range of 0.17-0.7 wt. % with respect to aromatics, the concentration of aromatics is in the range of 0.62-2.5 wt. % with respect to solvent and the reactions were monitored in the time interval in the range of 15 min to 2 h.

A maximum conversion of substituted aromatics and yield of ring hydrogenated products were achieved without disturbing of substituents using HRO catalysts in aqueous medium under mild reaction conditions. 100% conversion of substituted aromatics such as phenol, anisole, benzoic acid, and aniline with 100% yield of ring hydrogenated products were achieved (Table 4, entry 1-5, example 20-24).

A maximum conversion of substituted aromatics and yield of ring hydrogenated products were achieved with reduction of substituent groups using HRO catalysts in aqueous medium under mild reaction conditions. 100% conversion of substituted aromatics such as benzaldehyde and acetophenone with 100% yield of ring and ring attached substituents hydrogenated products were achieved (Table 4, entry 7-8, example 26-27).

A maximum conversion of methyl-3-picolinate achieved using HRO supported catalysts in aqueous medium under mild reaction conditions. 100% yield of hydrogenation followed by hydrolysis product was achieved (Table 4, entry 6, example 25).

In particular, using lignin derived methoxy phenols, the reactions were performed at temperature in the range of 25-200° C. and with a hydrogen pressure in the range of 10-30 bar with continuous flow of $H_2$ (10-50 ml/min) through MFC, the ruthenium loading in the range of 0.17-0.35 wt. % with respect to methoxy phenols, the concentration of methoxy phenols is in the range of 2.5-6.25 wt. % with respect to solvent and the reactions were monitored in the time interval in the range of 1 h to 10 h. A maximum conversion of methoxy phenols and the yield of selective hydrodeoxygenated product were achieved using HRO supported catalysts in aqueous medium under mild reaction conditions. 100% conversion of methoxy phenols such as 2-methoxy phenol (guaiacol), 2,6-dimethoxy phenol (syringol), 3-methoxy phenol and 4-methoxy phenol with 70-100% yield of selective deoxygenated cyclohexanol product was achieved (Table 5, entry 1-10, example 28-37).

Continuous flow of $H_2$ showed better results compared with batch $H_2$ for hydrogeoxygenation of methoxy phenols rendering selective formation of cyclohexanol. Decreasing the flow rate of $H_2$ increased the selectivity of cyclohexanol (Table 5, entry 3, example 30 and Table 6, entry 6, example 38).

The catalytic activity of HRO/H-β was compared with other conventionally used catalysts such as 5% Ru/C, 5% Pt/C, 5% Pd/C and 65% Ni@$SiO_2Al_2O_3$ for selective hydrogeoxygenation of guaiacol to cyclohexanol. A set of the reactions were carried out at 160° C., 30 bar $H_2$, and using 10 wt. % of catalyst (with respect to guaiacol) for 2 h. The HRO/H-β catalyst showed better catalytic activity (100% conversion of guaiacol, 79% yield of cyclohexanol) than conventional catalysts—5% Ru/C (100% guaaiacol conversion, 65% yield of cyclohexanol), 5% Pt/C (90% guaaiacol conversion, 38% yield of cyclohexanol) 5% Pd/C (100% guaaiacol conversion, 6% yield of cyclohexanol and observed 2-methoxy cyclohexanol as major product (94%)) and 65% Ni@$SiO_2Al_2O_3$ (59% guaaiacol conversion, 49% yield of cyclohexanol) (Table 6, entry 1-6, example 38).

The active catalyst (HRO and its supported forms) was recycled and reused up to five reaction cycles without drop in its catalysts activity in the case of guaiacol to cyclohexanol and xylose to xylitol. The catalyst was recovered from the product mixture by simple centrifugation; the obtained solid was washed with water and dried at room temperature and used for the next cycle and the same procedure was repeated for five cycles and observed 100% yield of products in all cases (example 42 and 43)).

The hydrodeoxygenation of methoxyphenol to cyclohexanol reaction was scaled up for 2.5 g using 6.2 wt. % guaiacol in water that showed 95% yield of cycloexanol demonstrates the scalability of the process. The catalyst was removed from the product mixture by simple centrifugation, the obtained aqueous product mixture was extracted with dichloromethane (DCM).

The hydrogenation of xylose to xylitol reaction was scaled up for 5 g using 12.5 wt. % xylose in water that showed 100% yield of xylitol demonstrates the scalability of the process. The catalyst was removed from the product mixture by simple centrifugation, the obtained aqueous product mixture is evaporated by using at 100° C. for 12 h and recovered a white solid xylitol.

TABLE 1

Hydrogenation of alkenes

| S.No | Reactant | Product | Conv. (%) | Yield (%) | Example |
|---|---|---|---|---|---|
| 1 |  |  | 100 | 100 | 1 |
| 2 |  |  | 100 | 100 | 2 |

Reactions conditions:

S.No 1: 2 g of cyclohexene in 40 ml of $H_2O$, 10 mg of HRO, 80° C., 10 bar $H_2$, 5 min S.No 2: 2 g of α-angelica lactone in 40 ml of $H_2O$, 200 mg of HRO/Na-β, 70° C., 10 bar $H_2$, 1 h

TABLE 2

Hydrogenation of ketones

| S.No | Reactant | Product | Conv. (%) | Yield (%) | Example |
|---|---|---|---|---|---|
| 1 | 2-hexanone | 2-hexanol | 100 | 100 | 3 |
| 2 | cyclohexanone | cyclohexanol | 100 | 100 | 4 |
| 3 | 4-methyl-2-pentanone | 4-methyl-2-pentanol | 100 | 100 | 5 |
| 4 | 2-butanone | 2-butanol | 100 | 100 | 6 |
| 5 | acetone | isopropanol | 100 | 100 | 7 |
| 6 | 2-butanone | 2-butanol | 100 | 100 | 8 |
| 7 | 2-butanone | 2-butanol | 100 | 70 | 9 |
| 8 | 2-butanone | 2-butanol | 100 | 100 | 10 |

Reactions conditions:
S.No 1-4: 1 g of ketones in 40 ml of $H_2O$, 50 mg of HRO/Na-β, 100° C., 15 bar $H_2$, 30 min
S.No 5: 5 g of acetone in 40 ml of $H_2O$, 250 mg of HRO/Na-β, 100° C., 30 bar $H_2$, 1 h
S.No 6: 1 g of 2-butanone in 40 ml of $H_2O$, 100 mg of HRO/Na-β, 100° C., 15 bar $H_2$, 30 min
S.No 7: 1 g of 2-butanone in 40 ml of $H_2O$, 30 mg of HRO/Na-β, 100° C., 15 bar $H_2$, 30 min
S.No 8: 1 g of 2-butanone in 40 ml of $H_2O$, 5 mg of HRO, 100° C., 15 bar $H_2$, 30 min

TABLE 3

Hydrogenation of aldehydes

| S.No | Reactant | Product | Conv. (%) | Yield (%) | Example |
|---|---|---|---|---|---|
| 1 | Glucose | Sorbitol | 100 | 100 | 11 |
| 2 | Mannose | Mannitol | 100 | 100 | 12 |

TABLE 3-continued

Hydrogenation of aldehydes

| S.No | Reactant | Product | Conv. (%) | Yield (%) | Example |
|---|---|---|---|---|---|
| 3 |  Xylose |  Xylitol | 100 | 100 | 13 |
| 4 |  Xylose |  Xylitol | 100 | 100 | 14 |
| 5 |  Xylose |  Xylitol | 0 | — | 15 |
| 6 |  Xylose |  Xylitol | 100 | 100 | 16 |
| 7 |  Xylose |  Xylitol | 60 | 60 | 17 |
| 8 |  Xylose |  Xylitol | 100 | 100 | 18 |
| 9 |  Furfural |  Furfuryl alcohol | 100 | 100 | 19 |

Reactions conditions:
S.No 1 and 2: 0.5 g of carbohydrates in 40 ml of $H_2O$, 50 mg of HRO/Na-β, 120° C., 20 bar $H_2$, 1 h
S.No 3: 0.5 g of xylose in 40 ml of $H_2O$, 50 mg of HRO/Na-β, 120° C., 20 bar $H_2$, 10 min
S.No 4: 0.5 g of xylose in 40 ml of $H_2O$, 50 mg of HRO/Na-β, 80° C., 20 bar $H_2$, 30 min
S.No 5: 0.5 g of xylose in 40 ml of $H_2O$, 50 mg of HRO/Na-β, 80° C., 2 bar $H_2$, 30 min
S.No 6: 5 g of xylose in 40 ml of $H_2O$, 250 mg of HRO/Na-β, 120° C., 50 bar $H_2$, 30 min
S.No 7: 8 g of xylose in 40 ml of $H_2O$, 400 mg of HRO/Na-β, 120° C., 50 bar $H_2$, 1 h
S.No 8: 0.4 g of xylose in 40 ml of $H_2O$, 20 mg of HRO/Na-β, 120° C., 20 bar $H_2$, 30 min
S.No 9: 1 g of furfural in 40 ml of $H_2O$, 100 mg of HRO/TiO$_2$, 150° C., 20 bar $H_2$, 3 h

TABLE 4

Hydrogenation of substituted aromatics

| S.No | Reactant | Product | Time | Conv. (%) | Yield (%) | Example |
|---|---|---|---|---|---|---|
| *Hydrogenation of aromatics-I* | | | | | | |
| 1 | phenol (OH) | cyclohexanol (OH) | 15 min | 100 | 100 | 20 |
| 2 | benzyl alcohol | cyclohexylmethanol | 1 h | 100 | 100 | 21 |
| 3 | anisole | methoxycyclohexane | 15 min | 100 | 100 | 22 |
| 4 | benzoic acid | cyclohexanecarboxylic acid | 2 h | 100 | 100 | 23 |
| 5 | aniline ($NH_2$) | cyclohexylamine ($NH_2$) | 1.5 h | 100 | 100 | 24 |
| *Hydrogenation of aromatics-II* | | | | | | |
| 6 | methyl nicotinate | piperidine-3-carboxylic acid | 1 h | 100 | 100 | 25 |
| *Hydrogenation of aromatics-III* | | | | | | |
| 7 | acetophenone | 1-cyclohexylethanol | 20 min | 100 | 100 | 26 |
| 8 | benzaldehyde | cyclohexylmethanol | 1 h | 100 | 100 | 27 |

Reactions conditions:
S.No 1: 1 g of phenol in 40 ml of $H_2O$, 50 mg of HRO/Na-, 70° C., 10 bar $H_2$
S.No 2-5: 1 g of aromatics in 40 ml of $H_2O$, 50 mg of HRO/Na-β, 100° C., 20 bar $H_2$
0.25 g of methyl nicotinate in 40 ml of $H_2O$, 50 mg of HRO/Na-β, 120° C., 15 bar $H_2$
S.No 7: 1 g of acetophenone in 40 ml of $H_2O$, 50 mg of HRO/Na-β, 100° C., 20 bar $H_2$
S.No 8: 1 g of benzaldehyde in 40 ml of $H_2O$, 50 mg of HRO/Na-β, 100° C., 20 bar $H_2$

TABLE 5

Hydrodeoxygenation of methoxy phenols

| S.No | Reactant | Product | Conv. (%) | Yield (%) | Example |
|---|---|---|---|---|---|
| 1 | guaiacol (2-methoxyphenol) | cyclohexanol | 100 | 86 | 28 |
| 2 | 2-methoxyphenol | cyclohexanol | 80 | 75 | 29 |
| 3 | 2-methoxyphenol | cyclohexanol | 100 | 95 | 30 |
| 4 | 2-methoxyphenol | cyclohexanol | 100 | 98-99 | 31 |
| 5 | 2-methoxyphenol | cyclohexanol | 100 | 99 | 32 |
| 6 | 2-methoxyphenol | cyclohexanol | 79 | 76 | 33 |
| 7 | 2-methoxyphenol | cyclohexanol | 100 | 95 | 34 |
| 8 | 2,6-dimethoxyphenol | cyclohexanol | 100 | 80 | 35 |
| 9 | 3-methoxyphenol | cyclohexanol | 100 | 85 | 36 |
| 10 | 4-methoxyphenol | cyclohexanol | 100 | 70 | 37 |

Reactions conditions:
S.No 1: 1 g of guaiacol in 40 ml of $H_2O$, 100 mg of HRO/H-β, 160° C., slow addition of $H_2$ through mass flow controller (MFC)-50 ml/min for 1 h
S.No 2: 1 g of guaiacol in 40 ml of $H_2O$, 100 mg of HRO/H-β, 160° C., slow addition of $H_2$ through mass flow controller (MFC)-20 ml/min for 2 h
S.No 3: 1 g of guaiacol in 40 ml of $H_2O$, 100 mg of HRO/H-β, 160° C., slow addition of $H_2$ through mass flow controller (MFC)-20 ml/min for 3 h
S.No 4: 1 g of guaiacol in 40 ml of $H_2O$, 100 mg of HRO/H-β, 160° C., slow addition of $H_2$ through mass flow controller (MFC)-10 ml/min for 6 h
S.No 5: 1 g of guaiacol in 40 ml of $H_2O$, 100 mg of HRO/H-β, 160° C., slow addition of $H_2$ through mass flow controller (MFC)-10 ml/min for 10 h
S.No 6: 1 g of guaiacol in 40 ml of $H_2O$, 50 mg of HRO/H-β, 160° C., slow addition of $H_2$ through mass flow controller (MFC)-10 ml/min for 6 h
S.No 7: 2.5 g of guaiacol in 40 ml of $H_2O$, 250 mg of HRO/H-β, 160° C., slow addition of $H_2$ through mass flow controller (MFC)-20 ml/min for 6 h
S.No 8-10: 1 g of methoxy phenols in 40 ml of $H_2O$, 100 mg of HRO/H-β, 160° C., slow addition of $H_2$ through mass flow controller (MFC)-10 ml/min for 6 h

TABLE 6

HRO catalyst comparison for hydrodeoxygenation of methoxy phenols

| S.No | Catalyst | Conv. (%) | Yield (%) Cyclohexanol | Yield (%) Others | Example |
|---|---|---|---|---|---|
| 1 | Blank | 0 | — | — | 38 |
| 2 | 5% Ru/C | 100 | 65 | 35 | 38 |
| 3 | 5% Pt/C | 90 | 38 | 52 | 38 |
| 4 | 5% Pd/C | 100 | 6 | 94 | 38 |
| 5 | 65% Ni@$SiO_2Al_2O_3$ | 59 | 49 | 10 | 38 |
| 6 | HRO/H-β | 100 | 75 | 25 | 38 |
| 7[b] | HRO/H-β | 100 | 79 | 21 | 39 |
| 8[c] | HRO/H-β | 0 | — | — | 40 |
| 9[d] | HRO/H-β | 100 | 87 | 13 | 41 |

Reaction conditions: 1 g of guaiacol in 40 ml of $H_2O$, 100 mg of catalyst, 160° C., 30 bar $H_2$, 2 h,
[b]–200° C.,
[c]–25° C.,
[d]–10 bar $H_2$ The following examples are given by way of illustrations and should not construed the scope of the invention.

EXAMPLES

Example: 1

To 2 g of cyclohexene in 40 ml of $H_2O$, HRO catalyst (10 mg) was added in a reactor vessel. The reactor vessel was then heated at 80° C. for 5 min under $H_2$ pressure (10 bar). After completion of the reaction, the catalyst was separated by using centrifuge and the obtained clear product mixture was analyzed by GC-MS. The reaction gave 100% conversion of cyclohexene with 100% yield of cyclohexane.

Example: 2

To 2 g of α-angelica lactone in 40 ml of $H_2O$, HRO/Na-β catalyst (200 mg) was added in a reactor vessel. The reactor vessel was then heated at 70° C. for 1 h under $H_2$ pressure (10 bar). After completion of the reaction, the catalyst was separated by using centrifuge and the obtained clear product mixture was analyzed by GC-MS. The reaction gave 100% conversion of α-angelica lactone with 100% yield of γ-valerolactone.

Example: 3

To 1 g of 2-hexanone in 40 ml of $H_2O$, HRO/Na-β catalyst (50 mg) was added in a reactor vessel. The reactor vessel was then heated at 100° C. for 30 min under $H_2$ pressure (15 bar). After completion of the reaction, the catalyst was separated by using centrifuge and the obtained clear product mixture was analyzed by GC-MS. The reaction gave 100% conversion of 2-hexanone with 100% yield of 2-hexanol.

Example: 4

To 1 g of cyclohexanone in 40 ml of $H_2O$, HRO/Na-β catalyst (50 mg) was added in a reactor vessel. The reactor vessel was then heated at 100° C. for 30 min under $H_2$ pressure (15 bar). After completion of the reaction, the catalyst was separated by using centrifuge and the obtained clear product mixture was analyzed by GC-MS. The reaction gave 100% conversion of cyclohexanone with 100% yield of cyclohexanol.

Example: 5

To 1 g of MIBK in 40 ml of $H_2O$, HRO/Na-β catalyst (50 mg) was added in a reactor vessel. The reactor vessel was then heated at 100° C. for 30 min under $H_2$ pressure (15 bar). After completion of the reaction, the catalyst was separated by using centrifuge and the obtained clear product mixture was analyzed by GC-MS. The reaction gave 100% conversion of MIBK with 100% yield of 4-methylpentan-2-ol.

Example: 6

To 1 g of 2-butanone in 40 ml of $H_2O$, HRO/Na-β catalyst (50 mg) was added in a reactor vessel. The reactor vessel was then heated at 100° C. for 30-min under $H_2$ pressure (15 bar). After completion of the reaction, the catalyst was separated by using centrifuge and the obtained clear product mixture was analyzed by GC-MS. The reaction gave 100% conversion of 2-butanone with 100% yield of 2-butanol.

Example: 7

To 1 g of acetone in 40 ml of $H_2O$, HRO/Na-β catalyst (250 mg) was added in a reactor vessel. The reactor vessel was then heated at 100° C. for 1 h under $H_2$ pressure (30 bar). After completion of the reaction, the catalyst was separated by using centrifuge and the obtained clear product mixture was analyzed by GC-MS. The reaction gave 100% conversion of acetone with 100% yield of isopropyl alcohol.

Example: 8

To 1 g of 2-butanone in 40 ml of $H_2O$, HRO/Na-β catalyst (100 mg) was added in a reactor vessel. The reactor vessel was then heated at 100° C. for 30 min under $H_2$ pressure (15 bar). After completion of the reaction, the catalyst was separated by using centrifuge and the obtained clear product mixture was analyzed by GC-MS. The reaction gave 100% conversion of 2-butanone with 100% yield of 2-butanol.

Example: 9

To 1 g of 2-butanone in 40 ml of $H_2O$, HRO/Na-β catalyst (30 mg) was added in a reactor vessel. The reactor vessel was then heated at 100° C. for 30 min under $H_2$ pressure (15 bar). After completion of the reaction, the catalyst was separated by using centrifuge and the obtained clear product mixture was analyzed by GC-MS. The reaction gave 70% conversion of 2-butanone with 70% yield of 2-butanol.

Example: 10

To 1 g of 2-butanone in 40 ml of $H_2O$, HRO catalyst (5 mg) was added in a reactor vessel. The reactor vessel was then heated at 100° C. for 30 min under $H_2$ pressure (15 bar). After completion of the reaction, the catalyst was separated by using centrifuge and the obtained clear product mixture was analyzed by GC-MS. The reaction gave 100% conversion of 2-butanone with 100% yield of 2-butanol.

Example: 11

To 0.5 g of glucose in 40 ml of $H_2O$, HRO/Na-β catalyst (50 mg) was added in a reactor vessel. The reactor vessel was then heated at 120° C. for 1 h under $H_2$ pressure (20 bar). After completion of the reaction, the catalyst was separated by using centrifuge and the obtained clear product mixture was analyzed by UHPLC. The reaction gave 100% conversion of glucose with 100% yield of sorbitol.

Example: 12

To 0.5 g of mannose in 40 ml of $H_2O$, HRO/Na-β catalyst (50 mg) was added in a reactor vessel. The reactor vessel was then heated at 120° C. for 1 h under $H_2$ pressure (20 bar). After completion of the reaction, the catalyst was separated by using, centrifuge and the clear product mixture was analyzed by UHPLC. The reaction gave 100% conversion of mannose with 100% yield of mannitol.

Example: 13

To 0.5 g of xylose in 40 ml of $H_2O$, HRO/Na-β catalyst (50 mg) was added in a reactor vessel. The reactor vessel was then heated at 120° C. for 10 min under $H_2$ pressure (20 bar). After completion of the reaction, the catalyst was separated by using centrifuge and the obtained clear product mixture was analyzed by UHPLC. The reaction gave 100% conversion of xylose with 100% yield of xylitol.

Example: 14

To 0.5 g of xylose in 40 ml of $H_2O$, HRO/Na-β catalyst (50 mg) was added in a reactor vessel. The reactor vessel was then heated at 80° C. for 30 min under $H_2$ pressure (20 bar). After completion of the reaction, the catalyst was separated by using centrifuge and the obtained clear product mixture was analyzed by UHPLC. The reaction gave 100% conversion of xylose with 100% yield of xylitol.

Example: 15

To 0.5 g of xylose in 40 ml of $H_2O$, HRO/Na-β catalyst (50 mg) was added in a reactor vessel. The reactor vessel was then heated at 80° C. for 30 min under $H_2$ pressure (2 bar). After completion of the reaction, the catalyst was separated by using centrifuge and the obtained clear product mixture was analyzed by UHPLC. The reaction gave no conversion, of xylose is observed.

Example: 16

To 5 g of xylose in 40 ml of $H_2O$, HRO/Na-β catalyst (250 mg) was added in a reactor vessel. The reactor vessel was then heated at 120° C. for 30 min under H₂ pressure (50 bar). After completion of the reaction, the catalyst was separated by using centrifuge and the obtained clear product mixture was analyzed by UHPLC. The reaction gave 100% conversion of xylose with 100% yield of xylitol.

Example: 17

To 8 g of xylose in 40 ml of H₂O, HRO/Na-β catalyst (400 mg) was added in a reactor vessel. The reactor vessel was then heated at 120° C. for 1 h under H₂ pressure (50 bar). After completion of the reaction, the catalyst was separated by using centrifuge and the obtained clear product mixture was analyzed by UHPLC. The reaction gave 60% conversion of xylose with 60% yield of xylitol.

Example: 18

To 0.4 g of xylose in 40 ml of H₂O, HRO/Na-β catalyst (20 mg) was added in a reactor vessel. The reactor vessel was then heated at 120° C. for 30 min under H₂ pressure (20 bar).
After completion of the reaction, the catalyst was separated by using centrifuge and the obtained clear product mixture was analyzed by UHPLC. The reaction gave 100% conversion of xylose with 100% yield of xylitol.

Example: 19

To 1 g of furfural in 40 ml of H₂O, HRO/TiO₂ catalyst (100 mg) was added in a reactor vessel. The reactor vessel was then heated at 150° C. for 3 h under H₂ pressure (20 bar). After completion of the reaction, the catalyst was separated by using centrifuge and the obtained clear product mixture was analyzed by GC-MS. The reaction gave 100% conversion of furfural with 100% yield of furfuryl alcohol.

Example: 20

To 1 g phenol in 40 ml of H₂O, HRO/Na-β catalyst (50 mg) was added in a reactor vessel. The reactor vessel was then heated at 70° C. for 15 min under H₂ pressure (10 bar). After completion of the reaction, the catalyst was separated by using centrifuge and the obtained clear product mixture was analyzed by GC-MS. The reaction gave 100% conversion of phenol with 100% yield of cyclohexanol.

Example: 21

To 1 g benzyl alcohol in 40 ml of H₂O, HRO/Na-β catalyst (50 mg) was added in a reactor vessel. The reactor vessel was then heated at 100° C. for 1 h under H₂ pressure (20 bar). After completion of the reaction, the catalyst was separated by using centrifuge and the obtained clear product mixture was analyzed by GC-MS. The reaction gave 100% conversion of benzyl alcohol with 100% yield of cyclohexylmethanol.

Example: 22

To 1 g anisole in 40 ml of H₂O, HRO/Na-β catalyst (50 mg) was added in a reactor vessel. The reactor vessel was then heated at 100° C. for 15 min under H₂ pressure (20 bar). After completion of the reaction, the catalyst was separated by using centrifuge and the obtained clear product mixture was analyzed by GC-MS. The reaction gave 100% conversion of anisole with 100% yield of methoxycyclohexane.

Example: 23

To 1 g benzoic acid in 40 ml of H₂O, HRO/Na-β catalyst (50 mg) was added in a reactor vessel. The reactor vessel was then heated at 100° C. for 2 h under H₂ pressure (20 bar). After completion of the reaction, the catalyst was separated by using, centrifuge and the obtained clear product mixture was analyzed by GC-MS. The reaction gave 100% conversion of benzoic acid with 100% yield of cyclohexanecarboxylic acid.

Example: 24

To 1 g aniline in 40 ml of H₂O, HRO/Na-β catalyst (50 mg) was added in a reactor vessel. The reactor vessel was then heated at 100° C. for 1.5 h under H₂ pressure (20 bar). After completion of the reaction, the catalyst was separated by using centrifuge and the obtained clear product mixture was analyzed by GC-MS. The reaction gave 100% conversion of aniline with 100% yield of cyclohexanamine.

Example: 25

To 0.25 g methyl nicotinate in 40 ml of H₂O, HRO/Na-β catalyst (50 mg) was added in a reactor vessel. The reactor vessel was then heated at 120° C. for 1 h under H₂ pressure (15 bar). After completion of the reaction, the catalyst was separated by using centrifuge and the obtained clear product mixture was analyzed by GC-MS. The reaction gave 100% conversion of aniline with 100% yield of piperidine-3-carboxylic acid.

Example: 26

To 1 g acetophenone in 40 ml of H₂O, HRO/Na-β catalyst (50 mg) was added in a reactor vessel. The reactor vessel was then heated at 100° C. for 20 min under H₂ pressure (20 bar). After completion of the reaction, the catalyst was separated by using centrifuge and the obtained clear product mixture was analyzed by GC-MS. The reaction gave 100% conversion of acetophenone with 100% yield of 1-cyclohexylethanol.

Example: 27

To 1 g benzaldehyde in 40 ml of H₂O, HRO/Na-β catalyst (50 mg) was added in a reactor vessel. The reactor vessel was then heated at 100° C. for 1 h under H₂ pressure (20 bar). After completion of the reaction, the catalyst was separated by using centrifuge and the obtained clear product mixture was analyzed by GC-MS. The reaction gave 100% conversion of benzaldehyde with 100% yield of cyclohexylmethanol.

Example: 28

To 1 g guaiacol in 40 ml of H₂O, HRO/H-Beta catalyst (100 mg) was added in a reactor vessel. The reactor vessel was then heated at 160° C. and H₂ was added at a flow rate of 50 ml/min though a mass flow controller (MFC) for 1 h under stirring. After completion of the reaction, the catalyst was separated by using centrifuge and the obtained clear product mixture was analyzed by GC-MS. The reaction gave 100% conversion of guaiacol with 86% yield of cyclohexanol.

Example: 29

To 1 g guaiacol in 40 ml of $H_2O$, HRO/H-β catalyst (100 mg) was added in a reactor vessel. The reactor vessel was then heated at 160° C. and $H_2$ was added at a flow rate of 20 ml/min though a mass flow controller (MFC) for 2 h under stirring. After completion of the reaction, the catalyst was separated by using centrifuge and the obtained clear product mixture was analyzed by GC-MS. The reaction gave 80% conversion of guaiacol with 75% yield of cyclohexanol.

Example: 30

To 1 g guaiacol in 40 ml of $H_2O$, HRO/H-β catalyst (100 mg) was added in a reactor vessel.
The reactor vessel was then heated at 160° C. and $H_2$ was added at a flow rate of 20 ml/min though a mass flow controller (MFC) for 3 h under stirring. After completion of the reaction, the catalyst was separated by using centrifuge and the obtained clear product mixture was analyzed by GC-MS. The reaction gave 100% conversion of guaiacol with 95% yield of cyclohexanol.

Example: 31

To 1 g guaiacol in 40 ml of $H_2O$, HRO/H-β catalyst (100 mg) was added in a reactor vessel. The reactor vessel was then heated at 160° C. and $H_2$ was added at a flow rate of 10 ml/min though a mass flow controller (MFC) for 6 h under stirring. After completion of the reaction, the catalyst was separated by using centrifuge and the obtained clear product mixture was analyzed by GC-MS. The reaction gave 100% conversion of guaiacol with 97-99% yield of cyclohexanol.

Example: 32

To 1 g guaiacol in 40 ml of $H_2O$, HRO/H-β catalyst (100 mg) was added in a reactor vessel. The reactor vessel was then heated at 160° C. and $H_2$ was added, at a flow rate of 10 ml/min though a mass flow controller (MFC) for 10 h under stirring. After completion of the reaction, the catalyst was separated by using centrifuge and the obtained clear product mixture was analyzed by GC-MS. The reaction gave 100% conversion of guaiacol with 99% yield of cyclohexanol.

Example: 33

To 1 g guaiacol in 40 ml of $H_2O$, HRO/H-β catalyst (50 mg) was added in a reactor vessel. The The reactor vessel was then heated at 160° C. and $H_2$ was added at a flow rate of 10 ml/min though a mass flow controller (MFC) for 6 h under stirring. After completion of the reaction, the catalyst was separated by using centrifuge and the obtained clear product mixture was analyzed by GC-MS. The reaction gave 79% conversion of guaiacol with 76% yield of cyclohexanol.

Example: 34

To 2.5 g guaiacol in 40 ml of $H_2O$, HRO/H-β catalyst (250 mg) was added in a reactor vessel. The reactor vessel was then heated at 160° C. and $H_2$ was added at a flow rate of 20 ml/min though a mass flow controller (MFC) for 6 h under stirring. After completion of the reaction, the catalyst was separated by using centrifuge and the obtained clear product mixture was analyzed by GC-MS. The reaction gave 100% conversion of guaiacol with 95% yield of cyclohexanol.

Example: 35

To 1 g syringol in 40 ml of $H_2O$, HRO/H-β catalyst (100 mg) was added in a reactor vessel. The reactor vessel was then heated at 160° C. and $H_2$ was added at a flow rate of 10 ml/min though a mass flow controller (MFC) for 6 h under stirring. After completion of the reaction, the catalyst was separated by using centrifuge and the obtained clear product mixture was analyzed by GC-MS. The reaction gave 100% conversion of guaiacol with 80% yield of cyclohexanol.

Example: 36

To 1 g 3-methoxy phenol in 40 ml of $H_2O$, HRO/H-β catalyst (100 mg) was added in a reactor vessel. The reactor vessel was then heated at 160° C. and $H_2$ was added at a flow rate of 10 ml/min though a mass flow controller (MFC) for 6 h under stirring. After completion of the reaction, the catalyst was separated by using centrifuge and the obtained clear product mixture was analyzed by GC-MS. The reaction gave 100% conversion of guaiacol with 85% yield of cyclohexanol.

Example: 37

To 1 g 4-methoxy phenol in 40 ml of $H_2O$, HRO/H-β catalyst (100 mg) was added in a reactor vessel. The reactor vessel was then heated at 160° C. and $H_2$ was added at a flow rate of 10 ml/min though a mass flow controller (MFC) for 6 h under stirring. After completion of the reaction, the catalyst was separated by using centrifuge and the obtained clear product mixture was analyzed by GC-MS. The reaction gave 100% conversion of guaiacol with 70% yield of cyclohexanol.

Example: 38

To 1 g guaiacol in 40 ml of $H_2O$, several catalysts comprising 5% Ru/C, 5% Pd/C, 5% Pt/C, 65% Ni@$SiO_2Al_2O_3$, and HRO/H-β catalysts (100 mg) was added in a reactor vessel besides carrying out the reaction without adding any catalyst. The reactor vessel was then heated at 160° C. for 2 h under $H_2$ pressure (30 bar). After completion of the reaction, the catalyst was separated by using centrifuge and the obtained clear product mixture was analyzed by GC-MS. In the absence of any catalyst, no conversion of guaiacol was observed while the catalysts gave following conversion and yields: 5% Ru/C (100% conversion with 65% yield of cyclohexanol), 5% Pd/C (100% conversion with 6% yield of cyclohexanol and 94% yield of 2-methoxy cyclohexanol), 5% Pt/C (90% conversion with 38% yield of cyclohexanol), 65% Ni@$SiO_2Al_2O_3$ (59% conversion with 49% yield of cyclohexanol), HRO/H-β (100% conversion with 75% yield of cyclohexanol).

Example: 39

To 1 g guaiacol in 40 ml of $H_2O$, HRO/H-β catalyst (100 mg) was added in a reactor vessel. The reactor vessel was heated at 200° C. for 2 h under $H_2$ pressure (30 bar). After completion of the reaction, the catalyst was separated by using-centrifuge and the obtained clear product mixture was analyzed by GC-MS. The reaction gave 100% conversion of guaiacol with 79% yield of cyclohexanol.

Example: 40

To 1 g guaiacol in 40 ml of $H_2O$, HRO/H-β catalyst (100 mg) was added in a reactor vessel. The reactor vessel was then heated at 25° C. for 2 h under $H_2$ pressure (30 bar). After completion of the reaction, the catalyst was separated by using centrifuge and the obtained clear product mixture was analyzed by GC-MS. The reaction gave no conversion of guaiacol.

Example: 41

To 1 g guaiacol in 40 ml of $H_2O$, HRO/H-β catalyst (100 mg) was added in a reactor vessel. The reactor vessel was then heated at 160° C. for 2 h under $H_2$ pressure (10 bar). After completion of the reaction, the catalyst was separated by using centrifuge and the obtained clear product mixture was analyzed by GC-MS. The reaction gave 100% conversion of guaiacol with 87% yield of cyclohexanol.

Example: 42

To 1 g guaiacol in 40 ml of $H_2O$, HRO/H-β catalyst (100 mg) was added in a reactor vessel. The reactor vessel was then heated at 160° C. for 3 h under slow addition of required amount of $H_2$ pressure (20 ml/min) though mass flow controller (MFC). After completion of the reaction, the catalyst was separated by using centrifuge and it was used as such for next cycle without any pre-treatment and this procedure was followed for five subsequent cycles. The catalyst activity did not change and all cycles gave 90-95% yield of cyclohexanol.

Example: 43

To 0.5 g of xylose in 40 ml of $H_2O$, HRO/Na-β catalyst (50 mg) was added in a reactor vessel. The reactor vessel was then heated at 120° C. for 10 min under $H_2$ pressure (20 bar). After completion of the reaction, the catalyst was separated by using centrifuge and it was used as such for next cycle without any pre-treatment and this procedure was followed for five subsequent cycles. The catalyst activity did not change and all cycles gave 97-100% yield of xylitol.

Example: 44

To 0.5 g xylose in 40 ml of $H_2O$, HRO/H-β catalyst (50 mg) was added in a reactor vessel. The reactor vessel was then heated at 100° C. for 30 min under slow addition of required amount of $H_2$ pressure (100 ml/min) though mass flow controller (MFC). After completion of the reaction, the catalyst was separated by using centrifuge and the obtained clear product mixture was analyzed by UHPLC. The reaction gave 10% conversion of xylose with 10% yield of xylitol.

The present invention discloses the utility of hydrous ruthenium oxide (HRO) as energy efficient reusable heterogeneous catalyst for hydrogenation of various organic molecules of industrial importance in aqueous medium under mild reaction conditions in shorter time and achieved maximum selectivity and yield of hydrogenated products. The present invention reports for the first time the use of HRO as heterogeneous catalyst for hydrogenation and hydrodeoxygenation of various organic molecules. The prior art cited above did not teach nor disclose the use of HRO as catalyst for hydrogenation of organic molecules under mild reaction conditions. In the present invention, the problem of separation of final product from the catalyst is made easier and less time consumed by the use of heterogeneous catalyst. The use of HRO reduces the reaction time making the process economical. Moreover the use of expensive metals like palladium, platinum and rhodium (Pd, Pt and Rh) along with Ru and use of hazardous solvent have been dispensed and the process is made benign. In the present invention the inventive step is the reduction of catalyst in situ and thus obviates the need of hydrogen for external reduction and thereby makes the process more energy efficient. Furthermore, this invention introduced addition of hydrogen by flow-controlled variable pressure mode which gives better selectivity of the desired product, in particular for cyclohexanol from methoxy phenols and renders safety.

ADVANTAGES OF THE INVENTION

Diverse reaction scope
Reactions under mild conditions
Nearly 100% conversion of organic molecules comprising alkenes, carbonyl compounds, and aromatics
Nearly 70-100% selectivity of the desired products
Better selectivity control of the desired product via flow-controlled variable pressure mode addition of H2 besides rendering process safety
Lesser reaction time
Lesser weight % of Ru
Higher wt. % of reactants
Does not require any catalyst prior reduction
Efficient recovery and reuse of the heterogeneous catalyst, in particular supported catalysts without any pretreatment

We claim:
1. A process for hydrogenation or/and hydrodeoxygenation of organic compound, wherein said process comprises:
  (i) mixing an organic compound in water at a temperature in the range of 24 to 28° C. in a reactor vessel to form a solution wherein the organic compound is used in a concentration in the range of 1 to 20 wt. % with respect to water;
  (ii) adding a catalyst to the solution obtained in (i) to obtain a mixture, wherein said catalyst is hydrous ruthenium oxide or supported hydrous ruthenium oxide;
  (iii) regulating pressure and increasing temperature of the reactor vessel in at least one of two modes, wherein the at least one of two modes comprises adding and removing $H_2$ into the mixture obtained in (ii) at 1-2 bar three times followed by adding $H_2$ to attain a pressure in the range of 2 to 50 bar in the reactor vessel; and heating the reactor vessel to a temperature ranging between 70 to 200° C. followed by stirring the reaction mixture at 600-1000 rpm after attaining temperature for a time period of 5 min to 6 h;
  (iv) cooling down the reactor vessel to a temperature in the range 25 to 28° C. and releasing unreacted $H_2$ and separating the catalyst to obtain a product mixture; and
  (v) separating product from the product mixture obtained in (iv) via direct solvent evaporation or by extractive separation to obtain an hydrogenated or/and hydrodeoxygenated organic compound.

2. The process as claimed in claim 1 wherein the organic compound is selected from the group consisting of an alkene, a carbonyl compound and an aromatic compound; wherein the alkene is selected from cyclohexene or α-angelica lactone; wherein the carbonyl compound is selected from the group consisting of furfural, glucose, mannose, xylose, acetone, cyclohexanone, 2-butanone, 2-hexanone and methyl isobutyl ketone; wherein the aromatic compound is selected from the group consisting of phenol, benzyl alcohol, anisole, aniline, methyl nicotinate, benzoic acid, benzaldehyde, acetophenone, methoxy phenol, guiacol and syringiol.

3. The process as claimed in claim 1, wherein the supported hydrous ruthenium oxide is supported with Na-β, H-β and $TiO_2$.

4. The process as claimed in claim 1, wherein the organic compound is used in a concentration in the range of 2 to 12.5 wt. %.

5. The process as claimed in claim 1, wherein conversion and yield of the hydrogenated or/and hydrodeoxygenated compound is in the range of 70 to 100%.

6. The process as claimed in claim 1, wherein the catalyst is reusable.

7. A process for hydrogenation or/and hydrodeoxygenation of organic compound, wherein said process comprises:
 (i) mixing an organic compound in water at a temperature in the range of 24 to 28° C. in a reactor vessel to form a solution wherein the organic compound is used in a concentration in the range of 1 to 20 wt. % with respect to water;
 (ii) adding a catalyst to the solution obtained in (i) to obtain a mixture, wherein said catalyst is hydrous ruthenium oxide or supported hydrous ruthenium oxide;
 (iii) regulating pressure and increasing temperature of the reactor vessel in at least one of two modes wherein the at least one of two modes comprises adding and removing $H_2$ into the mixture obtained in (ii) at 1-2 bar three times followed by heating the reactor vessel to attain a temperature ranging between 70 to 160° C.; and adding $H_2$ continuously into the reactor vessel at a flow rate ranging between 10-100 ml/min through a mass flow controller (MFC) while simultaneously stirring the mixture at 600-1000 rpm for 30 min to 10 hrs;
 (iv) cooling down the reactor vessel to a temperature in the range 25 to 28° C. and releasing unreacted $H_2$ and separating the catalyst to obtain a product mixture; and
 (v) separating product from the product mixture obtained in (iv) via direct solvent evaporation or by extractive separation to obtain a hydrogenated or/and hydrodeoxygenated organic compound.

8. The process as claimed in claim 7, wherein the organic compound is selected from the group consisting of an alkene, a carbonyl compound and an aromatic compound; wherein the alkene is selected from cyclohexene or α-angelica lactone; the carbonyl compound is selected from furfural, glucose, mannose, xylose, acetone, cyclohexanone, 2-butanone, 2-hexanone and methyl isobutylketone; and the aromatic compound is selected from phenol, benzyl alcohol, anisole, aniline, methyl nicotinate, benzoic acid, benzaldehyde, acetophenone, methoxy phenol, guiacol and syringiol.

9. The process as claimed in claim 7, wherein the supported hydrous ruthenium oxide is supported with Na-β, H-β and $TiO_2$.

10. The process as claimed in claim 7, wherein the organic compound is used in a concentration in the range of 2 to 12.5 wt. %.

11. The process as claimed in claim 7, wherein conversion and yield of the hydrogenated or/and hydrodeoxygenated compound is in the range of 70 to 100%.

12. The process as claimed in claim 7, wherein the catalyst is reusable.

* * * * *